United States Patent [19]

Asher et al.

[11] Patent Number: 5,217,461
[45] Date of Patent: Jun. 8, 1993

[54] APPARATUS FOR MAINTAINING VERTEBRAE IN A DESIRED SPATIAL RELATIONSHIP

[75] Inventors: Marc A. Asher, Leawood, Kans.; Charles F. Heinig, Ware Neck, Va.

[73] Assignee: Acromed Corporation, Cleveland, Ohio

[21] Appl. No.: 839,202

[22] Filed: Feb. 20, 1992

[51] Int. Cl.5 .............................................. A61F 5/00
[52] U.S. Cl. .................................... 606/61; 606/63
[58] Field of Search .......................... 606/53, 60–63, 606/67, 68

[56] References Cited

U.S. PATENT DOCUMENTS

| | | | |
|---|---|---|---|
| 2,579,968 | 12/1951 | Rush | 606/62 |
| 4,433,677 | 2/1984 | Ulrich et al. | 606/61 |
| 4,719,905 | 1/1988 | Steffee | 606/61 |
| 4,858,602 | 8/1989 | Seidel et al. | 606/60 |
| 4,931,055 | 6/1990 | Bumpus et al. | 606/61 X |
| 4,981,481 | 1/1991 | Kranz et al. | 606/62 |
| 4,998,936 | 3/1991 | Mehdian | 606/61 |
| 5,019,078 | 5/1991 | Perren et al. | 606/61 |
| 5,024,213 | 6/1991 | Asher et al. | 606/61 X |
| 5,074,864 | 12/1991 | Cozad et al. | 606/61 X |

FOREIGN PATENT DOCUMENTS

| | | | |
|---|---|---|---|
| 1127578 | 12/1984 | U.S.S.R. | 606/61 |
| 1256739 | 9/1986 | U.S.S.R. | 606/61 |

Primary Examiner—Richard J. Apley
Assistant Examiner—Linda C. M. Dvorak
Attorney, Agent, or Firm—Tarolli, Sundheim & Covell

[57] ABSTRACT

An apparatus for maintaining vertebrae in a desired spatial relationship in a spinal column includes an elongated one-piece rod which extends along the spinal column. An upper portion of the rod has a diameter which is less than the diameter of a lower portion of the rod. A first plurality of connector assemblies engage the lower portion of the rod and connect the lower portion of the rod to vertebrae. A second plurality of connector assemblies engage the upper portion of the rod and connect the upper portion of the rod to vertebrae which are disposed in the spinal column above the vertebrae to which the lower portion of the rod is connected.

7 Claims, 2 Drawing Sheets

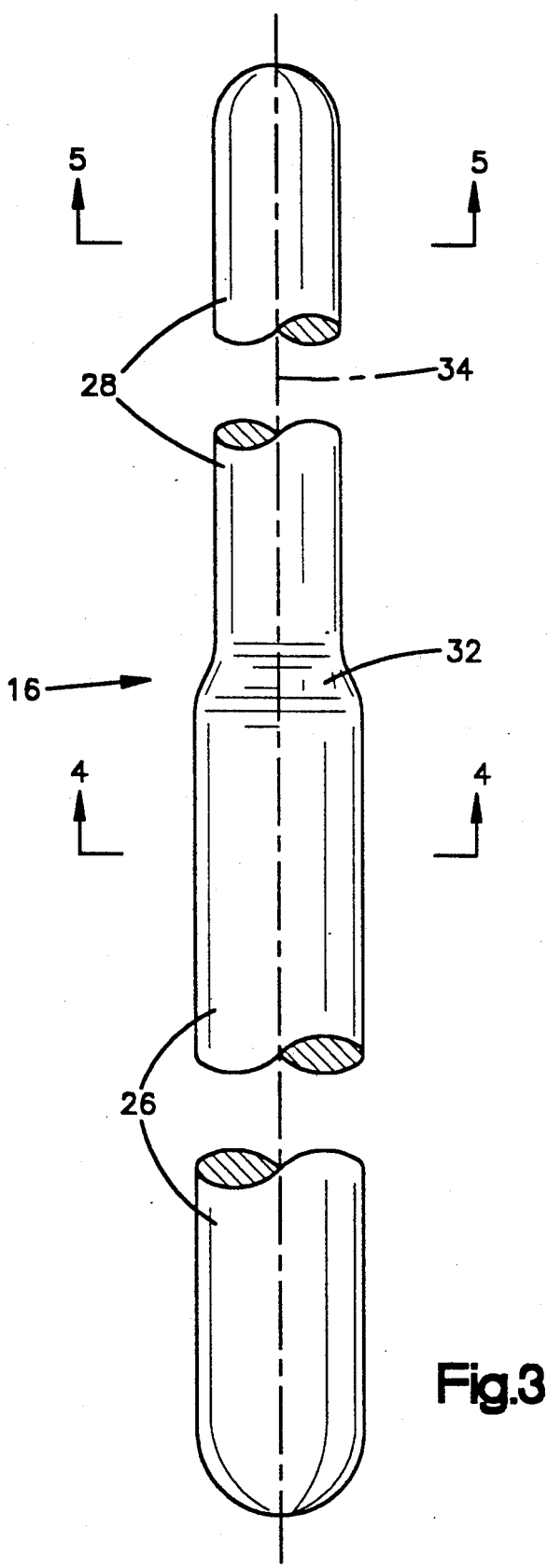
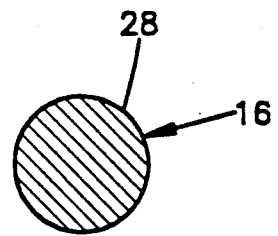
Fig.5
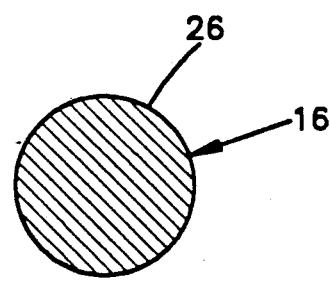
Fig.4
Fig.3

APPARATUS FOR MAINTAINING VERTEBRAE IN A DESIRED SPATIAL RELATIONSHIP

BACKGROUND OF THE INVENTION

The present invention relates to an apparatus which is implanted in a human body to correct a deformed and/or degenerated spinal column, and more specifically relates to an apparatus which holds vertebrae in the spinal column in a desired spatial relationship.

A known apparatus for maintaining vertebrae in a desired spatial relationship in a spinal column is disclosed in U.S. Pat. No. 4,648,388, issued Mar. 10, 1987 and entitled "Apparatus and Method for Maintaining Vertebrae in a Desired Relationship". This known apparatus includes an elongate, cylindrical rod which extends along the spinal column. Connector assemblies are provided to connect the cylindrical rod to vertebrae in the spinal column. The rod maintains the vertebrae in a desired position.

Typically, the cylindrical rod has one diameter throughout its length. As a result, the surgeon may be faced with using a rod smaller in diameter than desired for a part of the spine. For example, the thickness of tissue between first vertebrae and the skin is less than the thickness of the tissue between second vertebrae and the skin. As a result, a rod of one diameter which is to extend between the first and second vertebrae will have to have a diameter which is small enough to be positioned between the first vertebrae and the skin along with the associated connectors and fasteners. However, such a rod may not have as large a diameter as may be desired to assist in carrying load. Therefore, the surgeon must compromise the load carrying capability of the rod because of the space requirements.

SUMMARY OF THE INVENTION

The present invention comprises a cylindrical rod which minimizes the compromise which the surgeon must make as to load carrying capability because of space requirements. In essence, the present invention comprises a rod having at least two cylindrical portions of different diameters, i.e., one diameter relatively small and one diameter relatively large. Thus, the rod can be used to connect vertebrae effectively in situations where the space between certain of vertebrae and the skin dictate that a small diameter rod be used but where the space between certain other of the vertebrae and the skin enable a large diameter rod to be used for load carrying capability.

An improved apparatus in accordance with the present invention for maintaining vertebrae in a desired spatial relationship in a spinal column includes an elongated rod which extends along the spinal column. An upper portion of the rod extends along a plurality of vertebrae which are disposed in the spinal column above vertebrae along which a lower portion of the rod extends. The upper and lower portions of the rod have a cylindrical configuration. The diameter of the lower portion of the rod is larger than the diameter of the upper portion of the rod. Connector assemblies are provided to connect the upper and lower portions of the rod with the vertebrae.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 3 is a plan view of a one-piece rod used in the apparatus of FIGS. 1 and 2;

FIG. 4 is a sectional view, taken generally along the line 4—4 of FIG. 3; and

FIG. 5 is a sectional view, taken generally along the line 5—5 of FIG. 3.

DESCRIPTION OF THE PREFERRED EMBODIMENT

Figure 1:
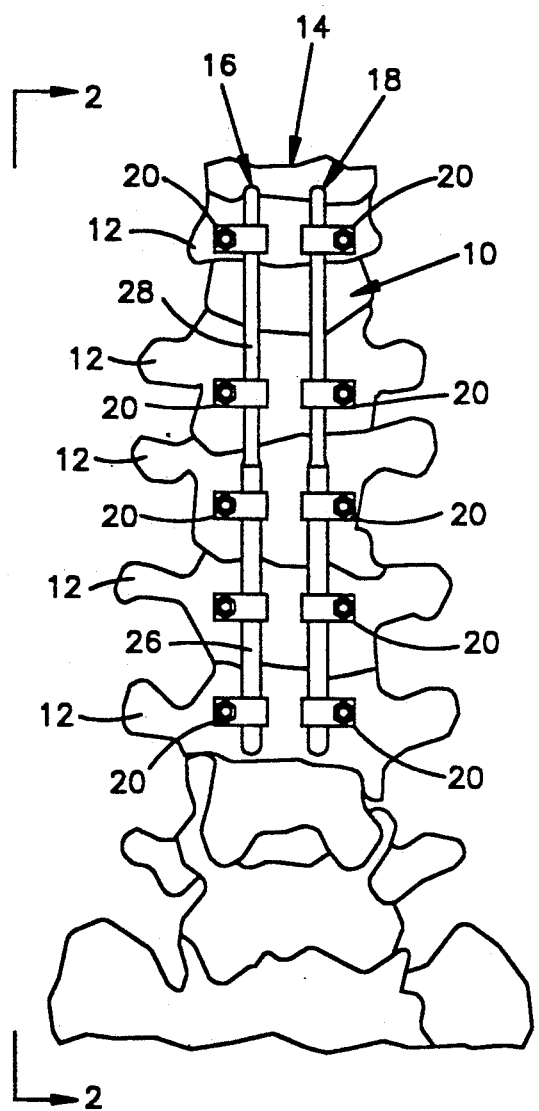
FIG. 1 is a posterior view of a human spinal column in which an apparatus constructed in accordance with the present invention has been implanted.
Figure 2:
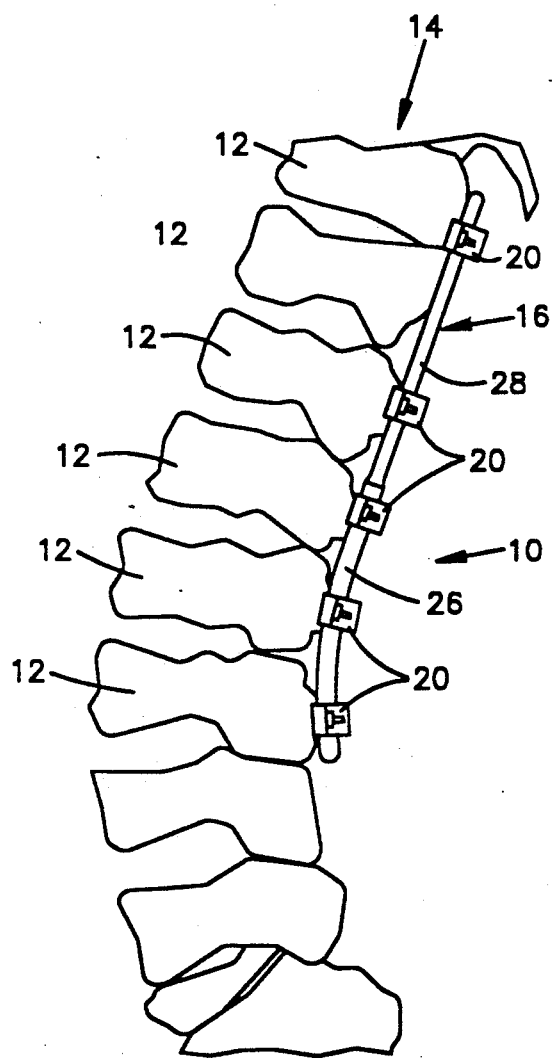
FIG. 2 is a left lateral view, taken generally along the line 2—2 of FIG. 1, further illustrating the relationship of the apparatus of FIG. 1 to the spinal column.

An apparatus 10 for maintaining vertebrae 12 in a desired spatial relationship in a human spinal column 14 is illustrated in FIGS. 1 and 2. The apparatus 10 includes a pair of elongate one-piece rods 16 and 18 which are connected with the spinal column 14 by connector assemblies 20. The connector assemblies 20 interconnect the rods 16 and 18 and the vertebrae 12 to hold the vertebrae in a desired spatial relationship relative to each other.

The rods 16 and 18 are formed as one-piece and are made of a uniform homogeneous composition throughout their length. The rods 16 and 18 are formed of a material which is satisfactory for implanting into the human body, such as stainless steel, titanium, or a composite.

The connector assemblies 20 include clamps which engage the rods 16 or 18 and screws which secure the clamps to the vertebrae. The connector assemblies may be constructed in the manner disclosed in U.S. Pat. No. 5,024,213, issued Jun. 18, 1981 or in U.S. Pat. No. 4,648,388, issued Mar. 10, 1987. However, it is contemplated that the connector assemblies 20 could have a different construction if desired. Regardless of the specific construction of the connector assemblies 20, each of the connector assemblies is effective to secure the rod 16 or 18 with one of the vertebrae 12 in the spinal column 14.

The rod 16 has a lower portion 26 which extends along a plurality of vertebrae 12 in a lower portion of the spinal column 14. The rod 16 also has an upper portion 28 which extends along a plurality of vertebrae which are disposed above the vertebrae along which the lower portion 26 of the rod extends.

In accordance with the present invention, the diameter of the lower portion 26 of the rod 16 is greater than the diameter of the upper portion 28 of the rod 16. Thus, the lower portion 26 (FIGS. 3 and 4) of the rod 16 has a cylindrical configuration and a first or relatively large diameter. The upper portion 28 (FIGS. 3 and 5) of the rod 16 also has a cylindrical configuration. However, the upper portion 28 of the rod 16 has a second or relatively small diameter. The upper and lower portions 26 and 28 of the rod 16 are coaxial.

By forming the upper portion 28 of the rod 16 with a smaller diameter than the lower portion 26, the upper portion of the rod can be more easily connected with the somewhat smaller vertebrae 12 which are disposed above the vertebrae to which the lower portion of the rod is connected. The mounting of the relatively large diameter lower portion 26 of the rod adjacent to vertebrae 12 in the lower portion of the spinal column is facilitated by the presence of a relatively large amount of soft tissue adjacent to the vertebrae 12 in the lower portion of the spinal column 14.

A circular junction 32 (FIG. 3) extends between the lower and upper portions 26 and 28 of the one-piece rod 16. The circular junction 32 tapers directly inwardly from the relatively large diameter lower portion 26 of the rod 16 to the relatively small diameter upper portion 28 of the rod. Thus, there is no significant length of the rod 16 between the relatively large diameter lower portion 26 and the relatively small diameter upper portion 28. The upper and lower portions 26 and 28 of the rod 16 and the circular junction 32 all have the same longitudinal central axis 34.

The junction between the lower and upper portions 26 and 28 could take a variety of forms. For example, there could be a circular concave surface of a given radius extending between the outer surfaces of the upper and lower portions. Also, a junction could be eliminated which would result in the rod having a shoulder surface extending perpendicular to the central axis 34.

Although the upper portion 28 of the rod 16 has a relatively small diameter compared to the lower portion 26 of the rod, the upper portion of the rod must have sufficient strength to hold the vertebrae 12 to which it is connected in place. In addition, the lower and upper portions 26 and 28 of the rod 16 must have sufficient flexibility to enable them to be bent to the desired configuration by a surgeon. However, the upper and lower portions 26 and 28 of the rod 16 must have sufficient stiffness so that they will maintain the configuration to which they are bent by the surgeon once the rod has been implanted in a spinal column. It has been determined that the diameter of the upper portion 28 of the rod 16 could be at least twenty percent (20%) less than the diameter of the lower portion 26 of the rod.

In one specific embodiment of the invention, the rod 16 has an overall length of eighteen inches. The lower portion 26 and the upper portion 28 both have a length of nine inches. In another embodiment of the invention, the rod 16 has an overall length of twenty-four inches. In this embodiment of the invention, the lower portion 26 and upper portion 28 both have a length of twelve inches. During an operation in which the rod 16 is implanted in the spinal column 14, the surgeon cuts the rod to the desired length. The surgeon may cut the rod 16 in such a manner that the lower portion 26 of the rod will be either longer or shorter than the upper portion 28 of the rod.

In one embodiment of the invention, the rod 16 is designed to have the lower portion 26 of the rod connected with lumbar vertebrae and the upper portion 28 of the rod connected with thoracic vertebrae. Thus, a plurality of connector assemblies 20 are utilized to connect the lower portion 26 of the rod 16 with a plurality of lumbar vertebrae 12. In this embodiment of the invention, a plurality of the connector assemblies 20 are also utilized to connect the upper portion 28 of the rod 16 with thoracic vertebrae 12. Since the thoracic vertebrae 12 are generally smaller than the lumbar vertebrae, the implanting of the rod 16 is facilitated by having the relatively large diameter lower portion 26 of the rod 16 engage the lumbar vertebrae and the relatively small diameter upper portion 28 of the rod 16 engage the thoracic vertebrae.

In this specific embodiment of the invention, the relatively large diameter lower portion 26 of the rod 16 has a diameter of one-quarter of an inch and is connected with a plurality of the lumbar vertebrae 12 by a plurality of the connector assemblies 20. The upper portion 28 of the rod 16 has a diameter of three-sixteenths of an inch and is connected with a plurality of the thoracic vertebrae by a plurality of the connector assemblies 20.

In a second embodiment of the invention, the rod 16 is designed to have the lower portion 26 of the rod connected with the thoracic vertebrae 12 and the upper portion 28 of the rod connected with the cervical vertebrae. Thus, a plurality of connector assemblies 20 are utilized to connect the lower portion 26 of the rod 16 with a plurality of thoracic vertebrae 12. In this embodiment of the invention, a plurality of connector assemblies 20 are also utilized to connect the upper portion 28 of the rod 16 with the cervical vertebrae 12. Since the cervical vertebrae 12 are generally smaller than the thoracic vertebrae, the implanting of the rod 16 is facilitated by having the large diameter lower portion 26 of the rod engage the thoracic vertebrae and the relatively small diameter upper portion 28 of the rod engage the cervical vertebrae.

In the second embodiment of the invention, the relatively large diameter lower portion 26 of the rod 16 has a diameter of three-sixteenths of an inch and is connected with a plurality of the thoracic vertebrae 12 by a plurality of the connector assemblies 20. The upper portion 28 of the rod 16 has a diameter of one-eighth of an inch and is connected with a plurality of the cervical vertebrae by a plurality of the connector assemblies 20.

It should be understood that the foregoing specific dimensions for the rod 16 have been set forth herein for purposes of clarity of description of specific embodiments of the rod. It is contemplated that other embodiments of the rod may have different dimensions. Although the illustrated embodiment of the rod 16 has only a large diameter portion 26 and a small diameter portion 28, it is contemplated that the rod could be constructed with portions having at least three different diameters. Thus, the rod 16 could be constructed with a relatively large diameter lower portion 26, an intermediate portion with a diameter which is smaller than the diameter of the lower portion, and an upper portion with a diameter which is smaller than the diameter of the intermediate portion.

The rod 18 has the same construction as the rod 16. The connector assemblies 20 all have the same construction. However, if desired, the connector assemblies 20 for the lower portion 26 of the rod 16 could have a different construction than the connector assemblies for the upper portion 28 of the rod.

In view of the foregoing description, it is apparent that the present invention provides an improved apparatus 10 for maintaining vertebrae 12 in a desired spatial relationship in a spinal column 14. The apparatus 10 includes an elongated rod 16 which extends along the spinal column 14. An upper portion 28 of the rod 16 extends along a plurality of vertebrae 12 which are disposed in the spinal column 14 above vertebrae along which a lower portion 26 of the rod extends. The upper and lower portions 26 and 28 of the rod 16 have a cylindrical configuration. The diameter of the lower portion 26 of the rod 16 is larger than the diameter of the upper portion 28 of the rod. Connector assemblies 20 are provided to connect the upper and lower portions 26 and 28 of the rod 16 with the vertebrae 12.

Since certain vertebrae are closer to the skin than other vertebrae, the rod of the present invention gives the surgeon the flexibility to use the small diameter portion for attachment to the vertebrae closer to the skin, and the larger diameter portion for attachment to the vertebrae further from the skin for load carrying capability.

Having described the invention, the following is claimed:

1. A spinal apparatus for maintaining vertebrae in a desired spatial relationship in a spinal column, said apparatus comprising an elongated one-piece rod which extends along the spinal column, said rod having a lower portion which extends along a first plurality of vertebrae and an upper portion which extends along a second plurality of vertebrae which are disposed in the spinal column above the first plurality of vertebrae, said lower portion of said rod having a substantially continuous cylindrical configuration with a first diameter, said upper portion of said rod having a substantially continuous cylindrical configuration with a second diameter which is less than the first diameter, a first plurality of connector assemblies including means for engaging the lower portion of said rod at a plurality of spaced apart locations along the lower portion of said rod and means for connecting the lower portion of said rod to vertebrae in the first plurality of vertebrae, and a second plurality of connector assemblies including means for engaging the upper portion of said rod at a plurality of spaced apart locations along the upper portion of said rod and means for connecting the upper portion of said rod to vertebrae in the second plurality of vertebrae.

2. An apparatus as set forth in claim 1 wherein the cylindrical upper and lower portions of said rod are disposed in a coaxial relationship.

3. An apparatus as set forth in claim 1 wherein said second diameter of the upper portion of said rod is at least 20% less than said first diameter of the lower portion of said rod.

4. An apparatus as set forth in claim 1 wherein the first diameter of the lower portion of said rod is one-quarter of an inch and the second diameter of the upper portion of said rod is three-sixteenths of an inch.

5. An apparatus as set forth in claim 1 wherein the first diameter of the lower portion of said rod is three-sixteenths of an inch and the second diameter of the upper portion of said rod is one-eighth of a inch.

6. An apparatus as set forth in claim 1 wherein at least some of the connector assemblies of said first plurality of connector assemblies connect the lower portion of said rod to lumbar vertebrae and at least some of the connector assemblies of said second plurality of connector assemblies connect the upper portion of said rod to thoracic vertebrae.

7. An apparatus as set forth in claim 1 wherein at least some of the connector assemblies of said first plurality of connector assemblies connect the lower portion of said rod to thoracic vertebrae and at least some of the connector assemblies of said second plurality of connector assemblies connect the upper portion of said rod to cervical vertebrae.

* * * * *